United States Patent [19]

Hua

[11] Patent Number: 5,108,749
[45] Date of Patent: Apr. 28, 1992

[54] SCALP TREATMENT COMPOSITION
[75] Inventor: Wang Y. Hua, Cheng Du, China
[73] Assignee: Jerry Y. Park, Houston, Tex.
[21] Appl. No.: 454,739
[22] Filed: Dec. 21, 1989

[30] Foreign Application Priority Data
Dec. 28, 1988 [CN] China .................. 881088609

[51] Int. Cl.$^5$ .................................. A61K 35/78
[52] U.S. Cl. .......................... 424/195.1; 424/526
[58] Field of Search ................. 424/195.1, 526

[56] References Cited
U.S. PATENT DOCUMENTS

| | | | |
|---|---|---|---|
| 3,932,611 | 1/1976 | McCar Thur | 424/70 |
| 4,002,734 | 1/1977 | Pickford | 424/196.1 |
| 4,230,689 | 10/1980 | Choy | 424/195.1 |

Primary Examiner—John W. Rollins
Attorney, Agent, or Firm—Neal J. Mosely

[57] ABSTRACT

A scalp treatment composition which promotes scalp and hair health and growth was developed in China and approved by medical authorities of the Peoples republic of China. The composition consists essentially of ginger (zingiber officianale), saffron (crocus sativus), root bark of shaggy-fruited dittany (orignum dictamnus), the roots of red-rooted salvia (clary or sage), cypress (cypressus sempervirens) leaves, xiang tong (cinnamornum camphora (linn) sieb.), Chinese angelica (aralia chinesis), Sichuan chili (cheilitis), bezoar (phytobezoar), artemisia argyi or Chinese mugworth, royal jelly (exudated queen bee), the dried rhizome of rehmannia (scrophulariacae), bear's gallbladder, lard (saturated animal fat), dragon's (daemonorops droco bl.), dragon's blood, gypsum (calcium sulfate), loess (yellowish greay Loam), radix (etymon root), salt (sodium chloride), tuber of multiflower knotweed (centaurer), Chuan poshi (cudrania cochinohinensis (lour) kudo et masam), blended together in a skin permeating agent, e.g., cudrania trienspidata (carr) bur. Through survey and clinical observation, it was found that the effectiveness of this composition to various alopecia reaches 96.82% and to hair loss caused by adipose ooze, 89.82%. The composition is non-poisonous, non harmful and has no side-effect. This composition was the first to pass the inspection of the Chinese Cosmetic Inspection Law since its enactment.

13 Claims, No Drawings

SCALP TREATMENT COMPOSITION

CLAIM OF PRIORITY

This application claims priority from patent application No. 88 1 08860 9 of the Peoples Republic of China.

FIELD OF THE INVENTION

This invention relates generally to a scalp treatment composition which promotes scalp and hair health and growth.

BRIEF DESCRIPTION OF THE PRIOR ART

The prior art includes many patents disclosing hair grooming compositions which illustrate the state of the art in herbal based compositions for promoting scalp and hair health and growth.

Edwards U.S. Pat. No. 604,111 discloses a hair tonic of mountain sage, glycerin, tincture of lobella, prickly pear juice, tincture of capsicum, sweet oil, and alcohol, which cleans the scalp, relaxes and stimulates the scalp, cools the scalp and gives the hair gloss.

McCarthur U.S. Pat. No. 3,932,611 discloses a composition for hair and scalp care comprising white petroleum jelly, beeswax, coconut oil, olive oil, castor oil, oil of sassafras and oil of cinnamon. The composition allegedly inhibits scaling of dandruff particles.

Pickford U.S. Pat. No. 4,002,734 discloses a composition for grooming or dressing hair comprising petroleum, rectified tar oil, phenol, sulfur, oxyquinoline, pine oil and castor oil in a petroleum jelly base. The composition allegedly inhibits scaling of dandruff particles.

Choy U.S. Pat. No. 4,230,689 discloses hydrating a mixture of rice with mung bean by heating at 75°–212° F. with a cup of Ginseng tea, recovering and condensing the vapors and using the condensate for grooming or dressing hair.

Faust U.S. Pat. No. 4,511,555 discloses a composition for grooming or dressing hair comprising an acceptable carrier, and a vegetable oil extract of sage, Indian hemp and rosemary. The composition is used in pomades and shampoos.

None of these compositions have received FDA approval in the U.S.

The present invention is distinguished over the prior art in general, and these patents in particular by providing a scalp treatment composition which promotes scalp and hair health and growth. This composition was developed in China and approved by medical authorities of the Peoples Republic of China. The composition consists essentially of ginger (zingiber officianale), saffron (crocus satures), root bark of shaggy-fruited dittany (orignam dictamnus), the roots of red-rooted salvia (clary or sage), cypress leaves (cypressus sempter-virens), xiang tong (cinnamornum camphora (linn) sieb.), Chinese angelica (aralia chinesis), Sichuan, chili (cheilitis), bezoar (phytobenzoai), artemisia argyi or Chinese mugworth, royal jelly (exudate of queen bee), the dried rhizome of rehmannia (scrophulariacal), bear's gallbladder, lard (saturated animal fat), dragon's blood (doemonorops draco bl.), gypsum (calcium sulfate), loess (yellowish grey loam), radix (etymorroot), salt (sodium chloride), tuber of multiflower knotweed (centaurer), Chuan poshi (cudrania cochinohinensis (lour) kudo et masam), blended together in a skin permeating agent, e.g., cudrania trienspidata (carr) bur. Through survey and clinical observation, it was found that the effectiveness of this composition to various alopecia reaches 96.82% and to hair loss caused by adipose ooze, 89.82%. The composition is non-poisonous, non harmful and has no side-effect. This composition was the first to pass the inspection of the Chinese Cosmetic Inspection Law since its enactment.

SUMMARY OF THE INVENTION

It is therefore an object of the present invention to provide a new and improved scalp treatment composition.

It is another object of this invention is to provide a new and improved scalp treatment composition which improves scalp health and hair growth.

Another object of this invention is to provide a new and improved scalp treatment composition which improves scalp health and promotes regrowth of hair in bald areas of the scalp.

Still another object of this invention is to provide a new and improved scalp treatment composition containing ginger, root bark of shaggy-fruited dittany, bezoar, bear's gallbladder, saffron, the roots of red-rooted salvia, Chinese angelica, tuber of multiflowered knotweed, radix rehmannia, blended together in a skin permeating agent.

Still another object of this invention is to provide a new and improved scalp treatment composition containing ginger, saffron, root bark of shaggy-fruited dittany, the roots of red-rooted salvia, cypress leaves, xiang tong, Chinese angelica, Sichuan chili, bezoar, artemisia argyi or Chinese mugworth and royal jelly, blended together with one or more of the ingredients the dried rhizome of rehmannia, bear's gallbladder, lard, dragon's blood, gypsum, loess, radix, salt, tuber of multiflower knotweed, Chuan poshi in a skin permeating agent.

A further object of this invention is to provide a new and improved scalp treatment composition containing ginger, saffron, root bark of shaggy-fruited dittany, the roots of red-rooted salvia, cypress leaves, xiang tong, Chinese angelica, Sichuan chili, bezoar, artemisia argyi or Chinese mugworth and royal jelly, blended together in a skin permeating agent, e.g., cudrania trienspidata (carr) bur.

A further object of this invention is to provide a new and improved scalp treatment composition containing ginger, saffron, root bark of shaggy-fruited dittany, the roots of red-rooted salvia, cypress leaves, xiang tong, Chinese angelica, Sichuan chili, bezoar, artemisia argyi or Chinese mugworth and royal jelly, blended together with one or more of the ingredients the dried rhizome of rehmannia, bear's gallbladder, lard, dragon's blood, gypsum, loess, radix, salt, tuber of multiflower knotweed, Chuan poshi in a skin permeating agent, e.g., cudrania trienspidata (carr) bur.

Other objects of the invention will become apparent from time to time throughout the specification and claims as hereinafter related.

DESCRIPTION OF A PREFERRED EMBODIMENT

This invention is involved with compounding a scalp treatment composition. Selected Chinese herbs, principally ginger, the root bark of shaggy-fruited dittany, natural bezoar, bear's gallbladder, saffron, tuber of multiflower knotweed, radix rehmannia, root of red-rooted salvia, and Chinese Angelica, after being ground, mixed, soaked and filtered, are compounded with a skin permeating agent made also from Chinese herbal medicines. A scalp treatment composition is obtained which then is prepared as a liquid and a special clinical effect to various alopecia such as hair loss caused by adipose ooze is obtained.

The purpose of this invention is achieved through the following method. Grind the Chinese herbs according to proportions, and then soak them in ethanol, in proportions of 1:1, at normal temperature (R.T.) and pressure (1.0 Atm.) for a selected period of time, e.g., 30-90 days. Then filter the mixture and the filtrate is then compounded with a skin permeating agent, e.g., cudrania trienspidata (carr) bur. A hair growth liquid is thus produced. Clinical testing of the composition is set forth below.

METHOD OF PREPARATION

The Chinese herbs and other ingredients used in this composition are ground finely and mixed in the following proportions: ginger 11-28, saffron 5-8, root bark of shaggy-fruited dittany 3-6; the roots of red-rooted salvia 5-9; cypress leaves 3-7; xiang tong (cinnamornum camphora (linn) sieb.); Chinese angelica 4-7; Sichuan chili 1-3; bezoar 2-5; artemisia argyi or Chinese mugworth 2-4; royal jelly 8-15; the dried rhizome of rehmannia 7-10; bear's gallbladder 2-4; lard 1-3; dragon's blood 1-3; gypsum 2-4; loess 1-3: radix 2-4; salt 1-3; tuber of multiflower knotweed 2-4 and Chuan poshi (cudrania cochinohinensis (lour) kudo et masam) 1-3. The proportions are by weight and total 100 in the finished composition.

The ground Chinese herbs are mixed according to the above proportions, and then soaked in ethanol, in proportions of 1:1, at normal temperature (R.T.) and pressure (1.0 Atm.) for a time of 30-90 days. Then the mixture is filtered and the filtrate is compounded with 10-15 parts of a skin permeating agent, e.g., cudrania trienspidata (carr) bur. to 85-90 parts of the herbs in the filtrate. A hair growth liquid is thus produced. Through survey and clinical observation, it has been found that the effectiveness of this liquid composition to various alopecia reaches 96.82% and to hair loss caused by adipose ooze, 89.82%. It is non-poisonous, non harmful and has no side-effect. The product may be supplied in solid from and dissolved by the user or may be supplied as a solution.

CLINICAL EVALUATION

The composition produced as described above was evaluated by various Chinese Health agencies under the proposed product name Fabi-S. The Observation Group of Fabi-S Sichuan West-China Chinese Medicine Institute reported as follows:

We have had further clinical observations on the hair-loss curing and preventing medicine—a scientific result donated to the Research Institute of Chinese Paining, which belongs to the Education, Science and Culture Branch of the All-China Social Welfare Center (now it is made over to China Kanghua, Sichuan Health Protection Article Company, the product is to be named Fabi-S) for one year and a month, since April 1987. The observation report about the prolonged curative effect of 212 various cases is ass follows:

1. Clinical Data:

212 cases: 212 cases totally under observation, 168 of male, 44 of female; 12-67 years old, 41.78 years old on the average; most are workers and cadres.

Classification of the Cases:

68 of hair-loss caused by adipose ooze, 74 of spotted alopecia, 26 of total alopecia, 44 of general alopecia.

Period of cases:

8 months-24 years, 8.42 years on the average.

2. Applying Method and Observation:

The patients apply Fabi-S twice per day externally, keeping up for over four weeks, and taking three months as a course of treatment. Make observation once every two weeks, putting down the statement, the days that the effect began to emerge and whether there are side effects from the use of it.

3. Appraisal Standards of Curative Effects:

a. Perfectly recover: Hair has grown completely;

b. Emerge effect: Hair grows partly, the area of hair-loss reduces;

c. Improve: The hair-loss is prevented, the dandruff is eliminated and the itch stops.

d. Has no effect: There is no change in the hair-loss location.

4. Result:

a. Hair-loss by Adipose Ooze:

68 cases were under observation. Most of them were caused by dermatitis ny adipose ooze. The affected part itches, and has much dandruff. More often, the head was bald around the top. Applying Fabi-S for 1-3 days, the itch stopped completely. Hair began to grow back in twenty days, and to turn thick and black in two months. Black hair grew fully in 5-12 months. A few of them recovered in only four months.

b. Hair-loss by Spotted Alopecia:

74 cases were under observation, more of them were diffuse. Applying Fabi-S for five days, new hair began to sprout, the hair-loss area reduced by and by. Most of them recovered in only 1-5 months.

c. Hair-loss by Total Alopecia:

26 cases were under observation, most of them lost their hair and eyebrow totally. Applying Fabi-S for ten days, the hair began to grow. All of them had their new hair and eyebrow in 2-6 months.

d. Hair-loss by General Alopecia:

44 cases were under observation. Applying Fabi-S for three days, the hair loss decreased, hair began to grow in seven days. All of them had their new hair in 2-6 months.

e. Has no effect to the hair loss caused by favus of the scalp, knife wound, burn and scald.

A tabulation of these results in more detail is as follows:

| Kind of Hair Loss | Number of cases | Recovery | Emergence of Effect | Improvement | No effect | Rate (%) |
|---|---|---|---|---|---|---|
| Hair Loss by Adipose Ooze | 68 | 46 | 10 | 5 | 7 | 89.79 |
| Spotted Alopecia | 74 | 73 | — | — | 1 | 98.64 |
| Total Alopecia | 26 | 24 | — | — | 2 | 92.30 |
| General Alopecia | 44 | 42 | — | — | 2 | 95.45 |
| Sum total | 212 | 185 | 10 | 7 | 12 | 94.33 |

CURATIVE EFFECT TABULATION OF 212 HAIR LOSS CASES

5. A brief introduction of typical cases

1). Nei Haifa; male, 64 years old, worker of Chengdu Seamless Steel Tube Works. Suffered from hair loss by adipose ooze for 24 years, had no effect through the treatment in many hospitals all over the country. Applying Fabi-S, new hair began to grow in 18 days. Keeping application up for eight months, new hair had grown fully over the head.

2). Li Guochang; male, 38 years old, actor in Chengdu. Suffered from hair loss by adipose ooze for five years. Applying Fabi-S for five months, black hair had regenerated completely.

3). Wu Guoping; male, 41 years old, managing director of Chengdu Clothing Factory. Suffered from hair loss by adipose ooze for 11 years. Applying Fabi-S for six months, new hair had grown fully over the head.

4). Tang Jing; male 35 years old, cadre of Supply and Marketing Cooperative. Suffered from spotted alopecia for four years, two thirds of the top of the head had been bald. Applying Fabi-S for twenty days, new hair sprouted. Keeping application up for six months, new hair had completely grown.

5). Zhou Ruqiong; female 24 years old, staff member of a trade company. Suffered from spotted alopecia for five years, little hair had remained. Applying Fabi-S for half a year, thick and black hair had regenerated.

6). Zeng Xiurong; female, 23 years old, staff member of catering trade. Suffered total alopecia for three years. Applying Fabi-S for six months, black hair had regenerated fully over the head.

7). Li Zhengming; male, 27 years old, staff member of a trade company. Suffered from general alopecia for four years. Applying Fabi-S for five months, black hair regenerated fully grown over the head.

8). Lai He; male; 26 years old, staff member of Emei Film Studio. Suffered from general alopecia for three years. Applying Fabi-S for five months, black hair had fully grown over the head.

TOXICOLOGIC TEST FOR FABI-S HAIR GROWING MEDICINE

Entrusted by China Kanghua Service Corporation, we had a toxicological test for Fabi-S according to "Appraisal Sequence and Method of Safety of Cosmetics" GB19-87. The results are as follows:

1. Acute Oral Toxicity Test: Taken by M. M. Albula Orally LD50 1.11 ml. kg weight, belongs to nonpoisonous grade in fact.

2. Acute skin toxicity test: No death or poisoning reaction emerging when applied on the skin of R.N. albus with the dosage of 1.11 ml. kg weight, belongs to nonpoisonous grade in fact.

3. Skin irritation test: Be not irritant by the test applying once or repeatedly.

4. Eye irritation test for applying once: Be irritant without washing; be slight irritant after washing.

5. Skin allergy test: Be negative of the guinea pig skin allergy test.

6. Test of skin allergy caused by light: Be negative of the test of the rabbit skin allergy caused by light.

While this invention has been shown fully and completely with special emphasis on certain preferred embodiments, it should be understood that within the scope of the appended claims the invention may be practiced otherwise than as specifically described herein.

I claim:

1. An intermediate composition for use in preparation of a scalp treatment composition comprising the following components:
   ginger 11-28, saffron 5-8, root bark of shaggy-fruited dittany 3-6, the roots of red-rooted salvia 5-9, Chinese angelica 4-7, bezoar 2-5, bear's gallbladder 2-3, radix 2-4, tuber of multiflower knotweed 2-4,
   the proportions being by weight and totaling 100 in the finished composition.

2. A composition according to claim 1 additionally containing:
   cypress leaves, xiang tong (cinnamornum camphora (linn) sieb.), Sichuan chili, artemisia argyi or Chinese mugworth, royal jelly, the dried rhizome of rehmannia, lard, dragon's blood, gypsum, loess, salt, and Chuan poshi (cudrania cochinohinensis (lour) kudo et masam), the composition having the following proportions:
   ginger 11-28, saffron 5-8, root bark of shaggy-fruited dittany 3-6, the roots of red-rooted salvia 5-9, cypress leaves 3-7, xiang tong 3-6 (cinnamornum camphora (linn) sieb.), Chinese angelica 4-7, Sichuan chili 1-3, bezoar 2-5, artemisia argyi or Chinese mugworth 2-4, royal jelly 8-15, the dried rhizome of rehmannia 7-10, bear's gallbladder 2-4, lard 1-3, dragon's blood 1-3, gypsum 2-4, loess 1-3, radix 2-4, salt 1-3, tuber of multiflower knotweed 2-4, and Chuan poshi 1-3 (cudrania cochinohinensis (lour) kudo et masam),
   the proportions are by weight and total 100 in the finished composition.

3. A scalp treatment composition
   produced by alcohol extraction of the composition of claim 2, and
   blended together in cudrania trienspidata (carr) bur. as a skin permeating agent.

4. A scalp treatment composition
   produced by alcohol extraction of the composition of claim 1, and
   blended together in cudrania trienspidata (carr) bur. as a skin permeating agent.

5. A method of producing a scalp treatment composition comprising
   grinding and mixing in the following proportions:
   ginger 11-28, saffron 5-8, root bark of shaggy-fruited dittany 3-6, the roots of red-rooted salvia 5-9, Chinese angelica 4-7, bezoar 2-5, bear's gallbladder 2-3, radix 2-4, tuber of multiflower knotweed 2-4,
   the proportions being by weight and totaling 100 in the finished composition, soaking the mixture in alcohol for 30-90 days and then the mixture, and
   blending the filtrate with a skin penetrating agent.

6. A method according to claim 5 in which
   the soaking of said mixture in alcohol is carried out at normal temperature and pressure.

7. A method according to claim 5 in which
   the composition produced is in solid form as pellets.

8. A method according to claim 5 in which
   the composition produced is in solution.

9. A method of producing a scalp treatment composition comprising
   grinding and mixing in the following proportions:
   ginger 11-28, saffron 5-8, root bark of shaggy-fruited dittany 3-6, the roots of red-rooted salvia 5-9, cypress leaves 3-7, xiang tong 3-6 (cinnamornum camphora (linn) sieb.), Chinese angelica 4-7, Sichuan chili 1-3, bezoar 2-5, artemisia argyi or Chinese mugworth 2-4, royal jelly 8-15, the dried rhizome of rehmannia 7-10, bear's gallbladder 2-4, lard 1-3, dragon's blood 1-3, gypsum 2-4, loess 1-3, radix 2-4, salt 1-3, tuber of multiflower knotweed 2-4, and Chuan poshi 1-3 (cudrania cochinohinensis (lour) kudo et masam), the proportions being by weight and totaling 100 in the finished composition, soaking the mixture in alcohol for 30-90 days and then the mixture, and blending the filtrate with a skin penetrating agent.

10. A method of promoting hair and scalp health and hair growth in bald areas of the scalp which comprises applying the scalp treatment composition of claim 4 to areas of the scalp requiring treatment in dosage quantities for a time sufficient to cause retardation of baldness and growth of hair.

11. A method of promoting hair and scalp health and hair growth in bald areas of the scalp which comprises applying the scalp treatment composition of claim 4 to areas of the scalp requiring treatment in dosage quantities for a time up to six months sufficient to cause retardation of baldness and growth of hair.

12. A method of promoting hair and scalp health and hair growth in bald areas of the scalp which comprises applying the scalp treatment composition of claim 3 to areas of the scalp requiring treatment in dosage quantities for a time sufficient to cause retardation of baldness and growth of hair.

13. A method of promoting hair and scalp health and hair growth in bald areas of the scalp which comprises applying the scalp treatment composition of claim 3 to areas of the scalp requiring treatment in dosage quantities for a time up to six months sufficient to cause retardation of baldness and growth of hair.

* * * * *